(12) United States Patent
Cho et al.

(10) Patent No.: US 9,403,874 B2
(45) Date of Patent: Aug. 2, 2016

(54) PEPTIDES AND USE THEREOF

(71) Applicants: IL YANG PHARM. CO.,LTD., Yongin-si (KR); INDUSTRY-ACADEMIC COOPERATION FOUNDATION, SOOKMYUNG WOMEN'S UNIVERSITY, Seoul (KR); SAMSUNG LIFE PUBLIC WELFARE FOUNDATION, Seoul (KR)

(72) Inventors: Dae Ho Cho, Seoul (KR); Min Kyung Jung, Seoul (KR); Soo Gyeong Ha, Seoul (KR); Jeong Min Park, Suwon-si (KR); Jin Young Lee, Seoul (KR); Sang Yoon Kim, Seoul (KR); Seung Beom Park, Seoul (KR); Hee Jong Kim, Asan-si (KR); Hyun Soo Ju, Cheongju-si (KR); Si Nae Lee, Yongin-si (KR); Hae Kyoung Lim, Yongin-si (KR); Sa Ik Bang, Seoul (KR)

(73) Assignees: SAMSUNG LIFE PUBLIC WELFARE FOUNDATION, Seoul (KR); IL YANG PHARM. CO., LTD., Gyeonggi-Do (KR); INDUSTRY-ACADEMIC COOPERATION FOUNDATION, SOOKMYUNG WOMEN'S UNIVERSITY, Seoul (KR)

( * ) Notice: Subject to any disclaimer, the term of this patent is extended or adjusted under 35 U.S.C. 154(b) by 107 days.

(21) Appl. No.: 14/412,020

(22) PCT Filed: Jul. 3, 2013

(86) PCT No.: PCT/KR2013/005912
§ 371 (c)(1),
(2) Date: Dec. 30, 2014

(87) PCT Pub. No.: WO2014/007547
PCT Pub. Date: Jan. 9, 2014

(65) Prior Publication Data
US 2015/0175662 A1    Jun. 25, 2015

(30) Foreign Application Priority Data
Jul. 3, 2012    (KR) .......................... 10-2012-0072513

(51) Int. Cl.
*C07K 7/08* (2006.01)
*C07K 7/06* (2006.01)
*C07K 5/083* (2006.01)
*C07K 5/09* (2006.01)
*C07K 5/11* (2006.01)
*C07K 5/072* (2006.01)
*C07K 5/068* (2006.01)
*A23L 1/305* (2006.01)
*C07K 5/087* (2006.01)
*A61K 38/00* (2006.01)

(52) U.S. Cl.
CPC ................. *C07K 7/08* (2013.01); *A23L 1/3053* (2013.01); *C07K 5/06086* (2013.01); *C07K 5/06095* (2013.01); *C07K 5/06113* (2013.01); *C07K 5/081* (2013.01); *C07K 5/0812* (2013.01); *C07K 5/0815* (2013.01); *C07K 5/0817* (2013.01); *C07K 5/1019* (2013.01); *C07K 7/06* (2013.01); *A23V 2002/00* (2013.01); *A61K 38/00* (2013.01)

(58) Field of Classification Search
CPC ....................................................... C07K 7/08
See application file for complete search history.

(56) References Cited

U.S. PATENT DOCUMENTS

| 8,563,689 B1 | 10/2013 | Takashi et al. |
| 2002/0192780 A1 | 12/2002 | Sohn et al. |
| 2006/0210556 A1 | 9/2006 | Baldwin et al. |
| 2006/0211752 A1 | 9/2006 | Kohn et al. |

(Continued)

FOREIGN PATENT DOCUMENTS

| KR | 1020080029963 A | 4/2008 |
| WO | 2004/069875 A2 | 8/2004 |
| WO | 2006/108211 A1 | 10/2006 |

(Continued)

OTHER PUBLICATIONS

International Preliminary Report on Patentability corresponding to International Patent Application No. PCT/KR2013/005912, issued Jan. 6, 2015.
International Search Report with Written Opinion corresponding to International Patent Application No. PCT/KR2013/005912, mailed Oct. 16, 2013.

(Continued)

*Primary Examiner* — Amber D Steele
(74) *Attorney, Agent, or Firm* — Lathrop & Gage LLP; Brian C. Trinque; Jana A. Lewis

(57) ABSTRACT

The present invention relates to novel peptides and use thereof and more specifically is directed to a peptide with anti-inflammatory effect, a polynucleotide encoding the peptide, a pharmaceutical composition comprising the peptide or polynucleotide for preventing or treating inflammatory diseases, an anti-inflammatory drug, an over-the-counter (OTC) drug composition comprising the peptide for preventing or ameliorating inflammation, a health food composition for alleviating or ameliorating inflammation, a cosmetic composition for preventing or ameliorating inflammation, a method for treating inflammatory diseases, comprising administrating the pharmaceutical composition to the subject suspected of having inflammatory disease, a method for preparing a mimetic of the peptide and a method for designing the same.

15 Claims, 8 Drawing Sheets

(56) References Cited

U.S. PATENT DOCUMENTS

2009/0312243 A1  12/2009  Danese et al.
2012/0157395 A1   6/2012  Ibuki et al.

FOREIGN PATENT DOCUMENTS

WO    2009040084  A2   4/2009
WO    2011039584  A2   4/2011

OTHER PUBLICATIONS

Lin et al. (1980) "Analysis of dipeptide mixtures by the combination of ion-pair reversed-phase high-performance liquid chromatographic and gas chromatographic-mass spectrometric techniques," J. Chrom. 197:31-41.
Miller et al. (1955) "Chemical stability and metabolic utilization of asparagine peptides," Arch. Biochem. Biophys. 56 (1):11-21.
Extended European Search Report corresponding to Patent Application No. EP13812943.2, mailed Nov. 20, 2015, 7 pages.
NCBI, GenBank accession No. AAH55907.1 (Oct. 8, 2003).

Fig. 2
Control 
SIS-1 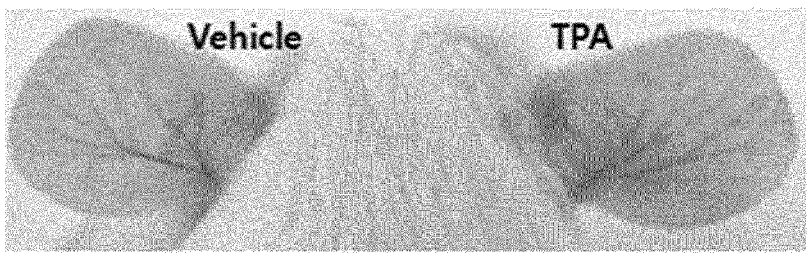
MTX 
DEX 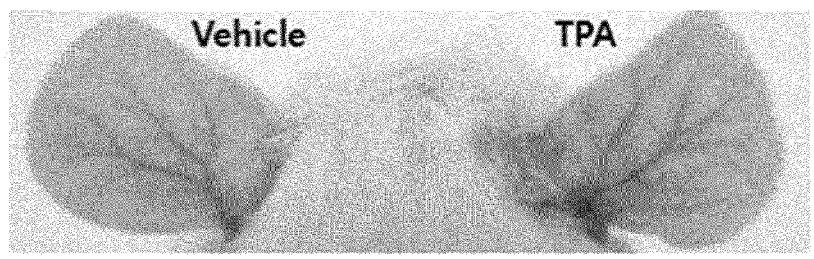

Fig. 4
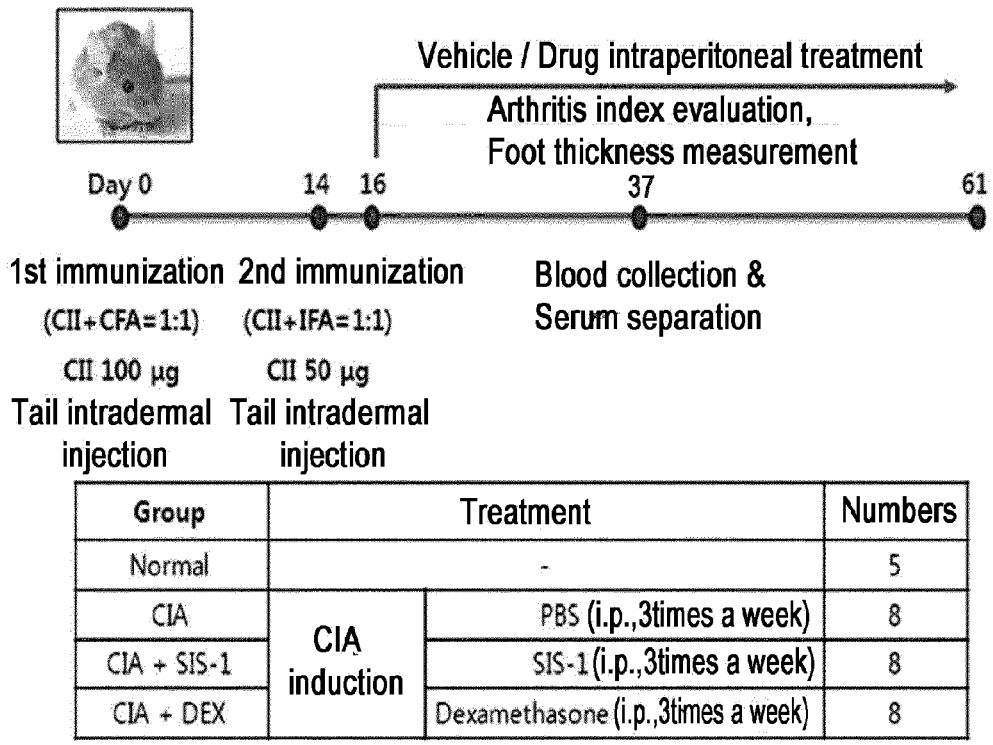
[Fig. 5]
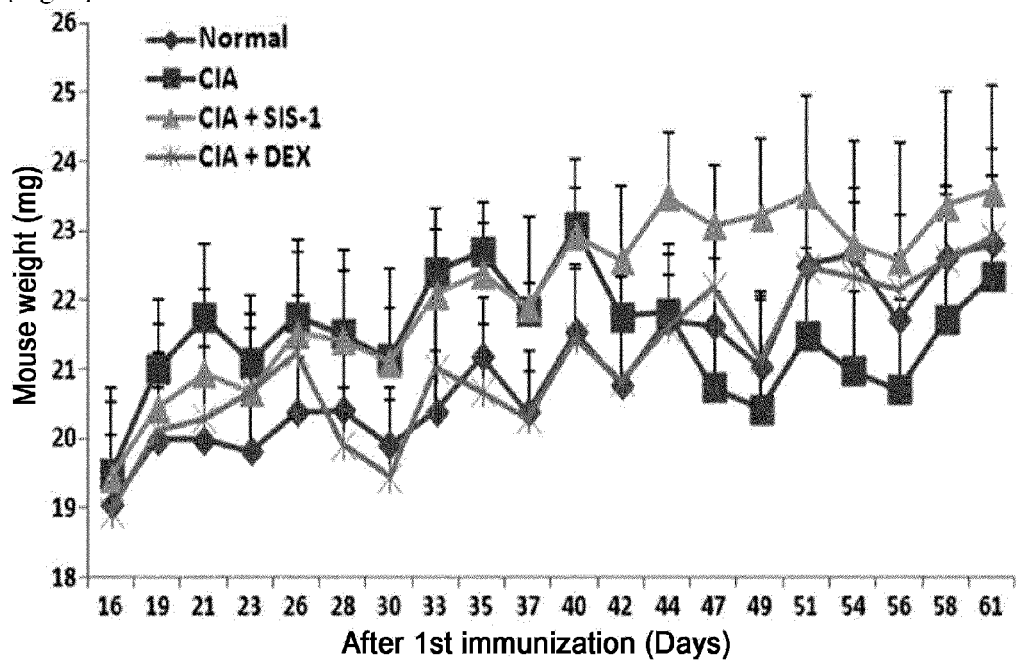

\#; P<0.001 *versus* the normal group
\*; P<0.05, \*\*; P<0.001 *versus* the CIA group

SEQUENCE LISTING

```
<160> NUMBER OF SEQ ID NOS: 18

<210> SEQ ID NO 1
<211> LENGTH: 19
<212> TYPE: PRT
<213> ORGANISM: Artificial Sequence
<220> FEATURE:
<223> OTHER INFORMATION: SIS-1 peptide

<400> SEQUENCE: 1

Met Ser Leu Pro Ser Pro Arg Asp Gly Arg Thr Asp Gly Arg Thr Asp
 1               5                  10                  15

Cys Thr Arg

<210> SEQ ID NO 2
<211> LENGTH: 6
<212> TYPE: PRT
<213> ORGANISM: Artificial Sequence
<220> FEATURE:
<223> OTHER INFORMATION: SIS-1#1 peptide

<400> SEQUENCE: 2

Met Ser Leu Pro Ser Pro
 1               5

<210> SEQ ID NO 3
<211> LENGTH: 7
<212> TYPE: PRT
<213> ORGANISM: Artificial Sequence
<220> FEATURE:
<223> OTHER INFORMATION: SIS-1#2 peptide

<400> SEQUENCE: 3

Arg Asp Gly Arg Thr Asp Gly
 1               5

<210> SEQ ID NO 4
```

```
<211> LENGTH: 6
<212> TYPE: PRT
<213> ORGANISM: Artificial Sequence
<220> FEATURE:
<223> OTHER INFORMATION: SIS-1#3 peptide

<400> SEQUENCE: 4

Arg Thr Asp Cys Thr Arg
  1               5

<210> SEQ ID NO 5
<211> LENGTH: 13
<212> TYPE: PRT
<213> ORGANISM: Artificial Sequence
<220> FEATURE:
<223> OTHER INFORMATION: SIS-1#4 peptide

<400> SEQUENCE: 5

Met Ser Leu Pro Ser Pro Arg Asp Gly Arg Thr Asp Gly
  1               5                  10

<210> SEQ ID NO 6
<211> LENGTH: 6
<212> TYPE: PRT
<213> ORGANISM: Artificial Sequence
<220> FEATURE:
<223> OTHER INFORMATION: SIS-1#5 peptide

<400> SEQUENCE: 6

Pro Ser Pro Arg Asp Gly
  1               5

<210> SEQ ID NO 7
<211> LENGTH: 10
<212> TYPE: PRT
<213> ORGANISM: Artificial Sequence
<220> FEATURE:
<223> OTHER INFORMATION: SIS-1#6 peptide

<400> SEQUENCE: 7

Pro Ser Pro Arg Asp Gly Arg Thr Asp Gly
  1               5                  10

<210> SEQ ID NO 8
<211> LENGTH: 4
<212> TYPE: PRT
<213> ORGANISM: Artificial Sequence
<220> FEATURE:
<223> OTHER INFORMATION: SIS-1#7 peptide

<400> SEQUENCE: 8

Arg Thr Asp Gly
  1

<210> SEQ ID NO 9
<211> LENGTH: 10
<212> TYPE: PRT
<213> ORGANISM: Artificial Sequence
<220> FEATURE:
<223> OTHER INFORMATION: SIS-1#8 peptide

<400> SEQUENCE: 9

Arg Asp Gly Arg Thr Asp Gly Arg Thr Asp
  1               5                  10

<210> SEQ ID NO 10
<211> LENGTH: 6
```

```
<212> TYPE: PRT
<213> ORGANISM: Artificial Sequence
<220> FEATURE:
<223> OTHER INFORMATION: SIS-1#9 peptide

<400> SEQUENCE: 10

Asp Gly Arg Thr Asp Gly
 1               5

<210> SEQ ID NO 11
<211> LENGTH: 5
<212> TYPE: PRT
<213> ORGANISM: Artificial Sequence
<220> FEATURE:
<223> OTHER INFORMATION: SIS-1#10 peptide

<400> SEQUENCE: 11

Gly Arg Thr Asp Gly
 1               5

<210> SEQ ID NO 12
<211> LENGTH: 3
<212> TYPE: PRT
<213> ORGANISM: Artificial Sequence
<220> FEATURE:
<223> OTHER INFORMATION: SIS-1#11 peptide

<400> SEQUENCE: 12

Thr Asp Gly
 1

<210> SEQ ID NO 13
<211> LENGTH: 2
<212> TYPE: PRT
<213> ORGANISM: Artificial Sequence
<220> FEATURE:
<223> OTHER INFORMATION: SIS-1#12 peptide

<400> SEQUENCE: 13

Asp Gly
 1

<210> SEQ ID NO 14
<211> LENGTH: 2
<212> TYPE: PRT
<213> ORGANISM: Artificial Sequence
<220> FEATURE:
<223> OTHER INFORMATION: SIS-1#13 peptide

<400> SEQUENCE: 14

Arg Asp
 1

<210> SEQ ID NO 15
<211> LENGTH: 3
<212> TYPE: PRT
<213> ORGANISM: Artificial Sequence
<220> FEATURE:
<223> OTHER INFORMATION: SIS-1#14 peptide

<400> SEQUENCE: 15

Arg Asp Gly
 1

<210> SEQ ID NO 16
<211> LENGTH: 4
<212> TYPE: PRT
```

```
<213> ORGANISM: Artificial Sequence
<220> FEATURE:
<223> OTHER INFORMATION: SIS-1#15 peptide

<400> SEQUENCE: 16

Arg Asp Gly Arg
 1

<210> SEQ ID NO 17
<211> LENGTH: 5
<212> TYPE: PRT
<213> ORGANISM: Artificial Sequence
<220> FEATURE:
<223> OTHER INFORMATION: SIS-1#16 peptide

<400> SEQUENCE: 17

Arg Asp Gly Arg Thr
 1               5

<210> SEQ ID NO 18
<211> LENGTH: 6
<212> TYPE: PRT
<213> ORGANISM: Artificial Sequence
<220> FEATURE:
<223> OTHER INFORMATION: SIS-1#17 peptide

<400> SEQUENCE: 18

Arg Asp Gly Arg Thr Asp
 1               5
```

PEPTIDES AND USE THEREOF

RELATED APPLICATIONS

This application is a 35 U.S.C. §371 filing of International Application No. PCT/KR2013/005912, filed Jul. 3, 2013, which claims priority to Korean Patent Application No. 10-2012-0072513, filed Jul. 3, 2012, each of which is incorporated herein by reference in its entirety.

TECHNICAL FIELD

The present invention relates to novel peptides and use thereof and more specifically is directed to a peptide with anti-inflammatory effect, a polynucleotide encoding the peptide, a pharmaceutical composition comprising the peptide or polynucleotide for preventing or treating inflammatory diseases, an anti-inflammatory drug, an over-the-counter (OTC) drug composition comprising the peptide for preventing or ameliorating inflammation, a health food composition for alleviating or ameliorating inflammation, a cosmetic composition for preventing or ameliorating inflammation, a method for treating inflammatory diseases, comprising administrating the pharmaceutical composition to the subject suspected of having inflammatory disease, a method for preparing a mimetic of the peptide and a method for designing the same.

BACKGROUND ART

Inflammation is a response occurred as a defensive action to minimize the body reaction and to recover the damaged area to its original state when the cell or tissue is damaged by any cause. Inflammation causes body reactions in nerves, blood vessels, lymph vessels, body fluid, and cells, resulting in pain, swelling, redness, and fever, thereby inducing dysfunction of body. The factors causing inflammation include physical causes such as injury, frostbite, burns, and radiation, chemical causes such as chemicals like acid, and immunological causes such as antibody reaction. Inflammation can also be caused by the imbalance of blood vessels and hormones. The cells damaged by external stimuli secrete various biological mediators such as pro-inflammatory cytokine, chemokine, interleukin, and interferon, thereby causing vasodilation, which in turn increases permeability and as a result, antibodies, complements, plasma and phagocytic cells gather at the site of inflammation. This phenomenon is the cause of erythema.

Drugs that act to remove the cause of inflammation and alleviate the body response and symptoms for removing inflammation are called anti-inflammatory drugs. To date, the substances used for the purpose of anti-inflammation include a non-steroid type such as ibuprofen and indomethacin, and a steroid type such as dexamethasone. However, the use of these substances has been limited due to safety problems. In this regard, there is a high need for the development of a safe anti-inflammatory drug with maximum effect and minimal side effects.

Inflammatory diseases which are associated with inflammation include atopy, psoriasis, dermatitis, allergy, arthritis, rhinitis, otitis media, pharyngolaryngitis, tonsillitis, cystitis, nephritis, pelvic inflammatory disease, Crohn's disease, ulcerative colitis, ankylosing spondylitis, systemic lupus erythematodes (SLE), atherosclerosis, asthma, arteriosclerosis, edema, rheumatoid arthritis, delayed allergy (IV-type allergy), graft rejection, graft-versus-host disease, autoimmune encephalomyelitis, multiple sclerosis, inflammatory bowel disease, arthritis, cystic fibrosis, diabetic retinopathy, rhinitis, ischemia-reperfusion injury, restenosis, glomerulonephritis, gastrointestinal allergy and the like.

The inflammatory diseases are known to be caused by various inflammatory cytokines.

Specifically, interleukin-6 (IL-6) is closely associated with systemic lupus erythematosus [Lupus. 2004; 13(5):339-343, Rationale for interleukin-6 blockade in systemic lupus erythematosus; J Rheumatol. 2010 January; 37(1):60-70, Interleukin 6 (IL-6) deficiency delays lupus nephritis in MRL-Faslpr mice: the IL-6 pathway as a new therapeutic target in treatment of autoimmune kidney disease in systemic lupus erythematosus], interleukin-4 (IL-4) or interleukin-12 (IL-12) is associated with atherosclerosis [Am J Pathol. 2003 September; 163(3): 1117-1125, The role of interleukin-4 and interleukin-12 in the progression of atherosclerosis in apolipoprotein E-deficient mice], interleukin-10 (IL-10), interferon-gamma (IFN-γ), interleukin-2 (IL-2), interleukin-1beta (IL-1β), IL-6, or tumor necrosis factor-alpha (TNF-α) is associated with pelvic inflammatory disease [Clin Chem Lab Med. 2008; 46(11):1609-1616, Significant elevation of a Th2 cytokine, interleukin-10, in pelvic inflammatory disease; Clin Chem Lab Med. 2008; 46(7):997-1003, Plasma interleukin-1beta, -6, -8 and tumor necrosis factor-alpha as highly informative markers of pelvic inflammatory disease], IL-4 or interleukin-5 (IL-5) is associated with asthma [J Allergy Clin Immunol. 2001 June; 107(6):963-970, Efficacy of soluble IL-4 receptor for the treatment of adults with asthma; Respir Res. 2001; 2(2):66-70. Epub 2001 Feb. 19, Th2 cytokines and asthma Interleukin-4: its role in the pathogenesis of asthma, and targeting it for asthma treatment with interleukin-4 receptor antagonists (Review); Curr Opin Allergy Clin Immunol. 2011 December; 11(6):565-70, Anti-interleukin-5 antibody therapy in asthma and allergies. (Review)], IL-4, IL-5 or IL-12 is associated with atopy or dermatitis [J Allergy Clin Immunol. 2001 September; 108(3):417-23, Immunostimulatory DNA inhibits IL-4-dependent IgE synthesis by human B cells; J Investig Allergol Clin Immunol 2007; Vol. 17(1): 20-26, Inhibition of Cytokine-Induced Expression of T-Cell Cytokines by Antihistamines], IL-2 or interleukin-8 (IL-8) is associated with psoriasis [Iranian J Publ Health, Vol. 36, No. 2, 2007, pp. 87-91, Th1/Th2 Cytokines in Psoriasis (REVIEW); Clin Exp Immunol. 1995 February; 99(2):148-54, IL-8/IL-8 receptor expression in psoriasis and the response to systemic tacrolimus (FK506) therapy], IL-6, IL-12 or interleukin-17 (IL-17) is associated with inflammatory bowel disease [World J Gastroenterol. 2008 Jul. 21; 14(27):4280-8, Role of cytokines in inflammatory bowel disease. (REVIEW); Gut. 2003 January; 52(1):65-70, Increased expression of interleukin 17 in inflammatory bowel disease], IL-1β is associated with ankylosing spondylitis [Formosan Journal of Rheumatology 2009; 23:40-46, The expression of pro-inflammatory cytokines and intracellular minerals in patients with ankylosing spondylitis], IL-12 is associated with multiple sclerosis [Proc Natl Acad Sci USA. 1997 Jan. 21; 94(2): 599-603, Increased interleukin 12 production in progressive multiple sclerosis: Induction by activated CD4+T cells via CD40 ligand], and IL-2 or IL-10 is associated with graft-versus-host disease [Curr Pharm Des. 2004; 10(11):1195-205, Anti-cytokine therapy for the treatment of graft-versus-host disease. (REVIEW); Blood. 2002 Oct. 1; 100(7):2650-8, Cytokine and chemokine profiles in autologous graft-versus-host disease (GVHD): interleukin 10 and interferon gamma may be critical mediators for the development of autologous GVHD]. Based on these findings, it is evident that the inflammatory cytokines are the important therapeutic target molecules in treatment of inflammatory diseases, and if the secretion of inflammatory cytokines can be reduced, the inflammatory diseases can be treated.

Meanwhile, rheumatoid arthritis is a representative disease of inflammatory diseases. Rheumatoid arthritis is a systemic inflammatory autoimmune disease which occurs in multiple joints. Unlike osteoarthritis which is caused by simple joint damage through friction, rheumatoid arthritis accompanies various immune responses including inflammatory responses occurred during the onset of disease. The first symptoms of rheumatoid arthritis are the activation of intra-articular synovial tissue cells and the infiltration and activation of inflammatory cells, which result in complex inflammatory responses in the intra-articular synovial tissue, cartilage and bone. These inflammatory responses cause symptoms like severe edema, erythema, and hot flash, and when these complications continue, the joint-forming tissues such as synovial tissue, ligaments, cartilage, bone and other tissues will be severely damaged. This finally leads to deformation, fracture, and dysfunction of joints. Rheumatoid arthritis is most common in age of 25 to 55 which are the productive ages, and thus enormous social and economic losses are expected and the quality of patients' lives is also expected to deteriorate due to the pain, fatigue, and depression caused by the disease.

Drugs that are currently used for treating many inflammatory diseases including rheumatoid arthritis are steroidal anti-inflammatory drugs such as dexamethasone, non-steroidal anti-inflammatory drugs such as aspirin and indomethacin, and anti-rheumatic drugs such as methotrexate. However, such drugs do not treat the source of disease. Also, steroid hormones have been used a lot as a medicine for arthritis, but as the side effects thereof become apparent, the use thereof has been limited. In addition, as rheumatoid arthritis causes severe pain in the patients for a long period of time, the patients should take anti-inflammatory drugs, but since many of anti-inflammatory drugs have potentially serious side effects, the caution should be taken for selecting and prescribing anti-inflammatory drugs in terms of dosage and term of use. Similarly, the existing chemotherapeutic drugs have drawbacks such as a variety of side effects that limit the long-term use of drug, a lack of anti-inflammatory effect, and a lack of therapeutic effects for the already developed arthritis. In addition, the mechanism behind the pathogenesis of rheumatic diseases has been recently identified at the cellular or molecular level. Thus for the treatment thereof, a use of biological drugs comprising the soluble receptors such as TNF-α, IL-1, and IL-6 produced by a recombinant DNA technology, as a therapeutic method targeting pro-inflammatory cytokine, has been increased, instead of using the empirical anti-rheumatic drugs. Recently, for the treatment of rheumatoid arthritis, a therapy of combining chemotherapeutic drugs represented by methotrexate which is the existing anti-rheumatic drug and biological drugs attracts attention, and thus the significance of biological drugs is growing in the market of arthritis drugs.

However, TNF-α formulation, which is a representative biological formulation for treating arthritis, is known to increase a risk of infection, and in particular, a risk of tuberculosis. In addition, TNF-α biological formulation is an expensive drug, which greatly burdens patients with medical expense. Also, it was reported that 20 to 30% of the patients were resistant to this formulation and they show no response to the treatment.

Therefore, there is a high demand for finding the solution to the above problems and for the development of a drug for inflammatory diseases including rheumatoid arthritis, having the therapeutic effects against acute inflammatory symptoms and pain. Most of the currently used drugs for inflammatory diseases have some side effects with various degrees of severity. Especially for the treatment of rheumatoid arthritis, a long-term administration of drug is required. Therefore, development of a drug with few side effects is very important.

DISCLOSURE OF INVENTION

Technical Problem

Hereupon, in efforts of developing the formulations for treating inflammatory diseases without side effects as a replacement for dexamethasone and methotrexate which have been used as a conventional medicine for treating inflammatory diseases, the present inventors have found that the novel peptides synthesized by the present inventors have an excellent anti-inflammatory effect by reducing the secretion of inflammatory cytokines and can treat edema and arthritis in animal model, thereby completing the present invention.

Solution to Problem

One objective of the present invention is to provide a novel isolated peptide.

Another objective of the present invention is to provide a polynucleotide encoding the peptide.

Another objective of the present invention is to provide a pharmaceutical composition for preventing or treating inflammatory diseases, comprising the peptide or the polynucleotide.

Another objective of the present invention is to provide an anti-inflammatory drug comprising the peptide or the polynucleotide.

Another objective of the present invention is to provide an over-the-counter (OTC) drug composition for preventing or ameliorating inflammation, comprising the peptide.

Another objective of the present invention is to provide a health food composition for alleviating or ameliorating inflammation, comprising the peptide.

Another objective of the present invention is to provide a cosmetic composition for preventing or ameliorating inflammation, comprising the peptide.

Another objective of the present invention is to provide a method for preparing a mimetic of the peptide.

Another objective of the present invention is to provide a method for designing a mimetic of the peptide.

Advantageous Effects of Invention

The novel peptide or fragment thereof of the present invention is a small peptide drug with excellent anti-inflammatory effect and few side effects. Thus, the novel peptide or fragment thereof is expected to replace the conventional drug for inflammatory diseases such as dexamethasone and methotrexate. Therefore, the peptide of the present invention can be used as a medicine for treating inflammatory diseases including autoimmune diseases. In addition, it can be used in a variety of products associated with alleviating inflammation such as OTC drug composition, health food composition, and cosmetic composition.

BRIEF DESCRIPTION OF DRAWINGS

FIG. 2 shows the photographs of TPA-induced ear edema mouse model demonstrating the changes in erythema and edema of TPA-induced mouse ear by administration of the peptide SIS-1 of the present invention.

FIG. 4 is a schematic diagram showing the test process and the test group of collagen-induced arthritis mouse model, which were conducted to determine the therapeutic effect of the peptide SIS-1 of the present invention against arthritis.

FIG. 5 shows the graph of periodical measurements of mouse weight after second immunization in the collagen-induced arthritis mouse model.

BEST MODE FOR CARRYING OUT THE INVENTION

Figure 1:
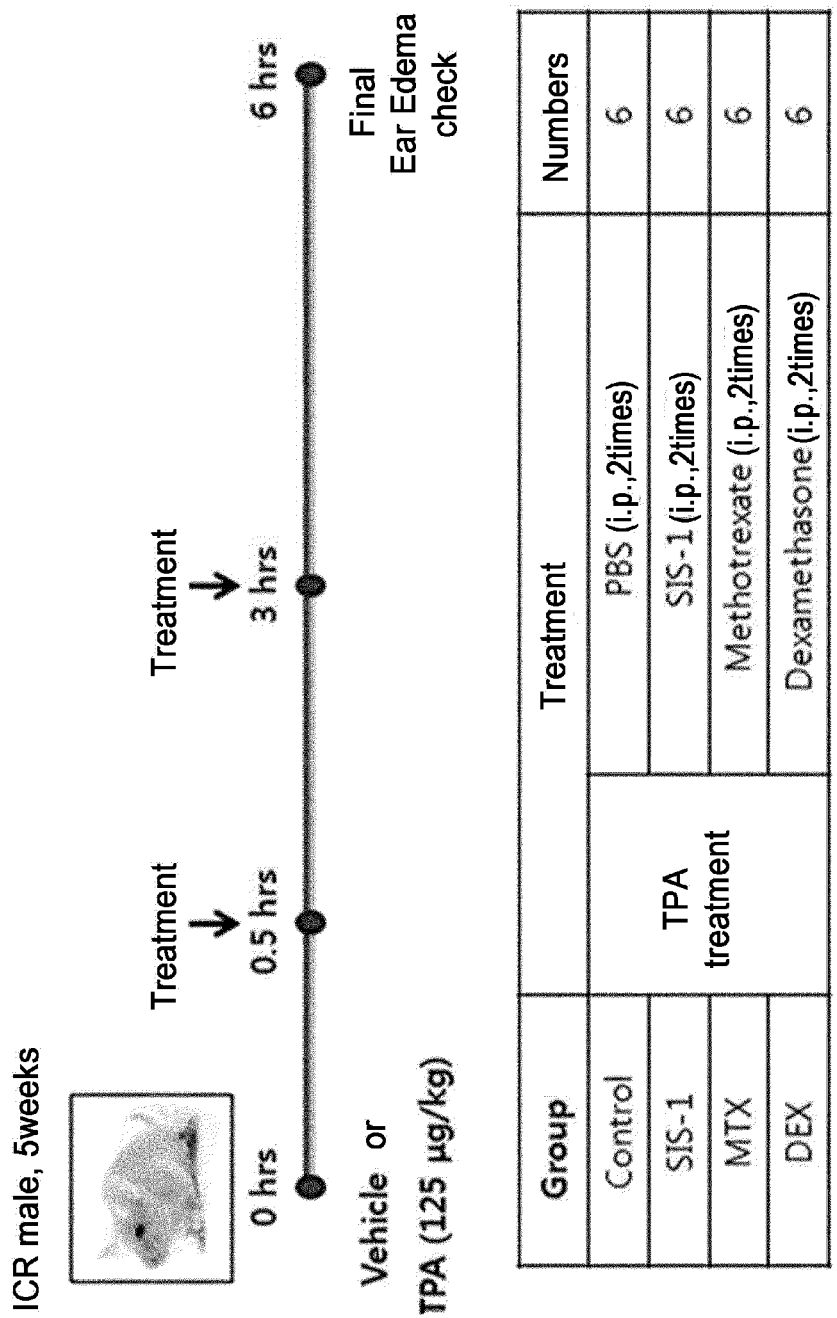
FIG. 1 is a schematic diagram showing the test process and the test group of TPA-induced ear edema mouse model, which were conducted to determine the anti-inflammatory effects of the peptide SIS-1 of the present invention.

As one aspect to achieve the above objectives, the present invention provides an isolated peptide represented by an amino acid sequence of SEQ ID NO: 1 or a fragment thereof.

The fragment comprises the fragments of an amino acid sequence of SEQ ID NO: 1 having the activity of treating or preventing inflammation, without limitation. For example, the fragment may be (i) a consecutive sequence of 6 to 13 amino acids, comprising the 4th to 6th amino acids (proline-serine-proline, PSP); (ii) a consecutive sequence of 4 to 10 amino acids, comprising the 10th to 13th amino acids (arginine-threonine-aspartic acid-glycine, RTDG); (iii) a consecutive sequence of 6 to 10 amino acids, comprising the 14th to 16th amino acids (arginine-threonine-aspartic acid, RTD); (iv) a consecutive sequence of 2 to 6 amino acids, comprising the 12th and 13th amino acids (aspartic acid-glycine, DG); or (v) a consecutive sequence of 2 to 6 amino acids, comprising the 7th and 8th amino acids (arginine-aspartic acid, RD) within an amino acid sequence of SEQ ID NO: 1. Alternatively, the fragment may be one of the amino acid sequences selected from the group consisting of SEQ ID NOs: 2 to 18.

Preferably, the peptide has an anti-inflammatory effect, including a peptide comprising the sequence or a fragment thereof without limitation.

A novel peptide of the present invention or a fragment thereof may comprise any one of the sequences selected from the SEQ ID NO: 1 to SEQ ID NO: 18 as follows.

```
SIS-1:    MSLPSPRDGRTDGRTDCTR (SEQ ID NO: 1)

SIS-1#1:  MSLPSP (SEQ ID NO: 2)

2:        RDGRTDG (SEQ ID NO: 3)

SIS-1#3:  RTDCTR (SEQ ID NO: 4)

SIS-1#4:  MSLPSPRDGRTDG (SEQ ID NO: 5)

SIS-1#5:  PSPRDG (SEQ ID NO: 6)

SIS-1#6:  PSPRDGRTDG (SEQ ID NO: 7)

SIS-1#7:  RTDG (SEQ ID NO: 8)

SIS-1#8:  RDGRTDGRTD (SEQ ID NO: 9)

SIS-1#9:  DGRTDG (SEQ ID NO: 10)

SIS-1#10: GRTDG (SEQ ID NO: 11)

SIS-1#11: TDG (SEQ ID NO: 12)

SIS-1#12: DG (SEQ ID NO: 13)

SIS-1#13: RD (SEQ ID NO: 14)

SIS-1#14: RDG (SEQ ID NO: 15)

SIS-1#15: RDGR (SEQ ID NO: 16)

SIS-1#16: RDGRT (SEQ ID NO: 17)

SIS-1#17: RDGRTD (SEQ ID NO: 18)
```

The amino acids mentioned herein are written as abbreviations according to IUPAC-IUB nomenclature as follows.
Alanine A Arginine R
Asparagine N Aspartic acid D
Cysteine C Glutamic acid E
Glutamine Q Glycine G
Histidine H Isoleucine I
Leucine L Lysine K
Methionine M Phenylalanine F
Proline P Serine S
Threonine T Tryptophan W
Tyrosine Y Valine V As used herein, the term "peptide or fragment thereof" refers to a polymer composed of 2 or more amino acids linked by amide bond (or peptide bond). For the purpose of the present invention, it refers to a peptide or fragment thereof demonstrating anti-inflammatory effect.

The peptide or fragment thereof of the present invention may comprise a targeting sequence, tag, labeled residue, and additional amino acid sequence designed for the specific purpose of increasing a half-life or stability of the peptide.

The peptide or fragment thereof of the present invention can be obtained by various methods well-known in the art. Specifically, it can be prepared by gene recombination and protein expression system, or by in vitro synthesis through chemical synthesis such as peptide synthesis and cell-free protein synthesis.

More specifically, the peptide or fragment thereof can be synthesized by well-known methods in the art, for example, an automated peptide synthesizer or genetic manipulation technology, but is not limited thereto. For example, the desired peptide can be generated by preparing a fusion gene encoding a fusion protein consisting of a fusion partner and the peptide of the present invention through genetic manipulation; transfecting a host microorganism with the same; expressing the same in the form of fusion protein in the host microorganism; and cleaving and isolating the peptide of the present invention from the fusion protein by using protease or compounds. For this method, DNA sequence encoding the amino acid residues that can be cleaved by protease, for example, Factor Xa or enterokinase or compound such as CNBr or hydroxylamine can be inserted in between a fusion partner and a gene for the peptide of the present invention.

According to one example of the present invention, the present inventors have identified that the 18 types of peptides reduce effectively the secretion of IL-1A, IL-1B, IL-2, IL-4, IL-5, IL-6, IL-8, IL-10, IL-12A, IL-13, IL-17A, GM-CSF or IL-34, which are the inflammatory cytokines, in activated B cells (Table 2). Then they have found that a representative peptide of the peptides, SIS-1 of SEQ ID NO: 1, alleviates edema in a mouse model of ear edema (FIGS. 2 and 3) and also alleviates arthritis in a mouse model of collagen-induced arthritis (FIGS. 5 to 10), thereby confirming that the peptides have anti-inflammatory effects. Also, the peptides having such anti-inflammatory effect were isolated and identified for the first time by the present inventor.

As another aspect, the present invention provides a polynucleotide encoding the peptide or fragment thereof.

As used herein for the purposes of describing a polynucleotide, the term "homology" is to indicate the degree of similarity of a sequence with a wild type amino acid sequence and a wild type nucleotide sequence. A homologous sequence includes the gene sequences which may be the same as a polynucleotide sequence encoding the peptide by 75% or more, preferably 85% or more, more preferably 90% or more, most preferably 95% or more. The comparison of homology is done with naked eyes or an easily available comparing program. Commercially available computer programs can calculate the homology between two or more sequences in percentage (%). Homology (%) can be calculated for adjacent sequences. The peptide can be generated in a large quantity by inserting the polynucleotide encoding the peptide into a vector and expressing the same.

As another aspect, the present invention provides a pharmaceutical composition for preventing or treating the inflammatory diseases, comprising the peptide or fragment thereof, or the polynucleotide.

The composition of the present invention may show the effect of preventing or treating inflammatory diseases by inhibition of the secretion of IL-1A, IL-1B, IL-2, IL-4, IL-5, IL-6, IL-8, IL-10, IL-12A, IL-13, IL-17A, GM-CSF or IL-34, which are the inflammatory cytokines known as therapeutic targets for inflammatory diseases. In one example of the present invention, it was identified that the 18 types of peptides of the present invention effectively reduce the secretion of IL-1A, IL-1B, IL-2, IL-4, IL-5, IL-6, IL-8, IL-10, IL-12A, IL-13, IL-17A, GM-CSF or IL-34 (Table 2), and also alleviate edema, which is a representative inflammatory disease, in animal model of edema (FIGS. 2 and 3), thereby confirming that the present peptides can treat inflammatory diseases by alleviating inflammation in the actual animal model. Furthermore, it was confirmed that the symptoms of arthritis were alleviated by treatment with the peptides of the present invention in the collagen-induced arthritis model (FIGS. 5 to 8). In histological analysis, the condition of the test model was maintained to be similar with that of a normal mice (FIG. 9), and the titer of autoantibodies was reduced serologically (FIG. 10), suggesting that the peptides can effectively treat autoimmune disease among inflammatory diseases. Thus, it was confirmed that the peptides of the present invention can be used as a pharmaceutical composition for preventing or treating inflammatory diseases.

As used herein, the term "Inflammatory disease" is a generic term for the diseases whose primary lesion is inflammation, and preferably may be atopy, psoriasis, dermatitis, allergy, arthritis, rhinitis, otitis media, pharyngolaryngitis, tonsillitis, cystitis, nephritis, pelvic inflammatory disease, Crohn's disease, ulcerative colitis, ankylosing spondylitis, systemic lupus erythematodes (SLE), atherosclerosis, asthma, arteriosclerosis, edema, rheumatoid arthritis, delayed allergy (IV-type allergy), graft rejection, graft-versus-host disease, autoimmune encephalomyelitis, multiple sclerosis, inflammatory bowel disease, cystic fibrosis, diabetic retinopathy, ischemia-reperfusion injury, restenosis, glomerulonephritis, or gastrointestinal allergy, and more preferably may be edema, rheumatoid arthritis, systemic lupus erythematodes (SLE), atherosclerosis, pelvic inflammatory disease, asthma, atopy, dermatitis, psoriasis, gastrointestinal allergy, ankylosing spondylitis, multiple sclerosis, or graft-versus-host disease, but is not limited thereto.

As used herein, the term "prevention" refers to any action to inhibit or delay the onset of inflammatory diseases by administration of the composition, and the term "treatment" refers to any action to alleviate or ameliorate the symptoms of inflammatory disease by administration of the composition.

The pharmaceutical composition of the present invention may comprise a pharmaceutically acceptable carrier, excipient, or diluent. As used herein, the term "pharmaceutically acceptable" refers to the amount enough to show therapeutic effects and the property of not causing side effects, and can be easily determined by those skilled in the art based on the factors well-known in the medical field such as a type of disease, the age, weight, health condition, gender, and sensitivity to drug of patient, route of administration, method of administration, the number of administration, duration of treatment, combination, or type of drug concurrently used.

A type of carrier that can be used in the present invention includes macromolecules that are slowly metabolized, such as liposome, polysaccharides, polylactic acid, poly glycolic acid, polymeric amino acids, and amino acid copolymers. For example, a pharmaceutically acceptable salt including a salt of inorganic acid such as hydrochloride, hydro-bromide, phosphate, and sulfate, and a salt of organic acid such as acetate, propionate, malonate, and benzoate; liquid including water, saline water, glycerol, and ethanol; and a supplementary substance including wettable powder, emulsifier, or pH buffer can be used. The information on a pharmaceutically acceptable carrier is disclosed in the literature [Remington's Pharmaceutical Sciences, Mack Publishing Company, 1991]. A composition comprising a pharmaceutically acceptable carrier may be in various formulations such as oral or parenteral formulation. When the composition is formulated, it can be prepared by using conventionally-used diluents such as fillers, extenders, binders, wetting agents, disintegrants, and surfactants, or excipients. Solid formulations for oral administration may include tablets, pills, powders, granules, and capsules. These solid formulations may be prepared by mixing one or more compounds and at least one of the excipients, for example, starch, calcium carbonate, sucrose or lactose, and gelatin. Also, in addition to a simple excipient, lubricants such as magnesium stearate and talc may be used. Liquid formulations for oral administration include suspensions, liquid, emulsion, and syrup, and may comprise various excipients, for example, wetting agents, sweeteners, fragrances, and preservatives, in addition to the commonly used simple diluents such as water and liquid paraffin. Formulations for parenteral administration may include sterile aqueous solutions, non-aqueous solvents, suspensions, emulsions, lyophilizing agents, and suppositories. Non-aqueous solvents and suspension solvents may be vegetable oils such as propylene glycol, polyethylene glycol, and olive oil; and injectable esters such as ethyl oleate. As a base for suppositories, witepsol, macrogol, tween 61, cacao butter, laurinum, and glycerogelatin may be used.

In addition, the pharmaceutical composition of the present invention may be in any one of the formulations selected from the group consisting of tablets, pills, powders, granules, capsules, suspensions, liquid, emulsion, syrup, sterile aqueous solutions, non-aqueous solvents, suspensions, emulsions, lyophilizing agents and suppositories.

In addition, the pharmaceutical composition of the present invention can be administered according to conventional methods in the pharmaceutical field by formulating it in a unit dosage form suitable for administration into the patient's body, preferably in a formulation useful for administration of peptide drugs, through oral route or parenteral route such as skin, intravenous, intramuscular, intra-arterial, intramedullary, intrathecal, intraventricular, pulmonary, transdermal, subcutaneous, intra-abdominal, intranasal, intra-alimentary, topical, sublingual, vaginal or rectal routes, using a conventional administration methods in the art, but is not limited thereto.

Also, the peptide can be used in combination with various pharmaceutically acceptable carriers such as saline water or organic solvents. Carbohydrate such as glucose, sucrose, or dextran; antioxidants such as ascorbic acid or glutathione; chelating agents; low molecular weight proteins; or other stabilizers may be used as drugs in order to increase the stability and absorption of the peptide.

A total effective amount of the composition of the present invention may be administered to patients in a single dose or in multiple doses for a long term by fractionated treatment protocol. The pharmaceutical composition of the present invention may have different content of active ingredients depending on the severity of disease. The desired total amount of the peptides of the present invention may be preferably about 0.0001 µg to 500 mg per day per 1 kg of patient's body weight, and most preferably 0.01 µg to 100 mg. However, an effective dose of the peptide for a patient is determined by considering not only the route of administration of a pharmaceutical composition and the number of treatments, but also many other factors such as the age, weight, health condition, and gender of patient, severity of disease, diet, and excretion rate. Thus, by considering these, those with ordinary skill in the art will be able to determine an appropriate effective dose of the composition of the present invention for its specific use. A pharmaceutical composition according to the present invention does not have any limitation on the type of formulation, route of administration and method of administration as long as it shows the effect of the present invention.

As another aspect, the present invention provides an anti-inflammatory drug comprising the peptide or fragment thereof, or the polynucleotide.

As another aspect, the present invention provides an over-the-counter (OTC) drug composition for preventing or ameliorating inflammation, comprising the peptide or fragment thereof.

Specifically, the composition of the present invention can be added to an OTC drug composition for the purpose of preventing or treating inflammatory diseases.

As used herein, the term "over-the-counter (OTC) drug" refers to one of the textile goods, rubber goods, or the like that are used for the purpose of treating, alleviating, removing, or preventing the disease in human or animal; a product that is neither a device or machine, or the like that acts weakly or indirectly on human body; a formulation used for sterilization, insecticide, and the like to prevent infection. That is, the OTC drug refers to the products that are used for the purpose of diagnosing, treating, alleviating, removing, or preventing the disease in human or animal, excluding a device, machine, and apparatus; and the products that are used for the purpose of providing pharmacological effects on the structure or function of human or animal excluding a device, machine, and apparatus.

When the peptide of the present invention is used as an additive to OTC drug, it can be added to the OTC drug as itself or used with other OTC drug or OTC drug ingredients. The present peptide can be used appropriately according to conventional methods. The amount of active ingredient to be added can be determined appropriately according to the purpose of use.

The OTC drug composition of the present invention may preferably be, but is not limited to, a sanitizer, shower foam, gargle, wipes, detergent, hand wash, humidifying filler, mask, ointment, or filter filler.

As another aspect, the present invention provides a health food composition for alleviating or ameliorating inflammation, comprising the peptide or fragment thereof.

More specifically, the peptide or fragment thereof of the present invention can be added to a health food composition for preventing or ameliorating inflammatory diseases.

When the peptide or fragment thereof of the present invention is used as an additive of health food, it can be added as itself or used with other health food or health food ingredients. The present peptide or fragment thereof can be used appropriately according to conventional methods. The amount of active ingredients to be added can be determined appropriately for the purpose of use.

A type of health food of the present invention is not particularly limited. The examples of the health food where the peptide can be added include meat, sausage, bread, chocolates, candies, snacks, sweets, pizza, ramen, and other noodles, gums, dairy products including ice cream, various soups, beverages, tea, drinks, alcoholic beverages, and vitamin complexes, including any type of health food in general meaning. The health food can also include feed for animals.

Aside from the above, the health food composition of the present invention may comprise a variety of nutritional supplements, vitamins, electrolytes, flavors, colorants, pectic acid and salts thereof, alginic acid and salts thereof, organic acid, protective colloidal thickeners, pH adjusting agents, stabilizers, preservatives, glycerin, alcohol, carbonizing agents used in soft drinks. In addition, the health food composition may comprise pulp for preparation of natural fruit juice, fruit juice beverage, and vegetable beverage.

As another aspect, the present invention provides a cosmetic composition for preventing or ameliorating inflammation, comprising the peptide or fragment thereof.

Specifically, the peptide or fragment thereof of the present invention can be added to a cosmetic composition for the purpose of preventing or ameliorating inflammation.

The cosmetic composition of the present invention can be prepared in a typical emulsified or solubilized formulation. A type of the emulsified formulation includes a nutritional toner, cream, and essence and the solubilized formulation may be a softening toner. An appropriate formulation of cosmetic composition may be, but is not limited to, a solution, gel, solid or paste-like anhydrous products, emulsions obtained by dispersing oil phase in water phase, suspensions, microemulsions, microcapsules, micro granulocytes or ion type (liposomes), bionic vesicular dispersants, cream, toner, lotion, powder, ointment, spray, or concealed stick. In addition, the cosmetic composition may be in a form of foam or aerosol composition comprising more of compressed propellant.

The cosmetic composition may additionally comprise fatty substances, organic solvents, solubilizers, thickening agents and gelling agents, softeners, antioxidants, suspending agents, stabilizers, foaming agents, fragrances, surfactants, water, ionic or non-ionic emulsifiers, fillers, sequestering agents, chelating agents, preservatives, vitamins, blocking agents, wetting agents, essential oils, dyes, pigments, hydrophilic or lipophilic activators, lipid vesicles, or any other ingredients commonly used in a cosmetic composition including conventionally-used supplements.

As another aspect, the present invention provides a method for treating inflammatory diseases, comprising administrating the pharmaceutical composition comprising the peptide or fragment thereof, or polynucleotide of the present invention to the subject suspected of having inflammatory disease.

In the present invention, the subject suspected of having inflammatory disease refers to the mammals including human, mouse, and domestic animals wherein the inflammatory diseases have occurred or may occur, but it includes any type of subjects that can be treated by the peptide of the present invention without limitation. A subject can be effectively treated by administrating the pharmaceutical composition comprising the peptide of the present invention to the subject suspected of having inflammatory disease. The inflammatory diseases are the same as described above.

As used herein, the term "administration" refers to introduction of the pharmaceutical composition of the present invention to a subject suspected of having inflammatory disease by any appropriate method, and the composition may be administered through various routes including oral or parenteral administration, as long as it can be delivered to a target tissue.

A method of treatment of the present invention may include the administration of a pharmaceutical composition comprising the peptide in a pharmaceutically effective amount. An appropriate total dosage per day can be determined by a doctor with appropriate medical judgment. Also, the composition may be administered in a single dose or several multiple doses. However, for the purpose of the present invention, it is preferable that a therapeutically effective amount for a specific patient is determined by various factors including a type and extent of response to be achieved, a specific composition for different cases, the age, weight, general health condition, and gender of patient, diet, duration of administration, route of administration and the excretion rate of composition, duration of treatment, a type of medications used together or concurrently with a specific composition, and other similar factors well-known in the medical field.

As another aspect, the present invention provides a method for preparing a mimetic of the peptide.

Specifically, the method for preparing a mimetic of the peptide may comprise designing a mimetic of the peptide with an anti-inflammatory activity from the peptide or fragment thereof; and synthesizing the designed mimetic of the peptide.

As used herein, the term "mimetic of peptide" or "peptidomimetic" refers to a compound which can mimic an intrinsic parent amino acid in protein, based on the fact that the substitution of an amino acid with the mimetic thereof does not affect significantly the activity of the protein. Thus it may refer to a compound that substitutes or modifies amino acid residues or peptide bond. The protein comprising a mimetic of the peptide is typically an inferior substrate to protease compared to a natural protein, and will have a longer activity invivo than a natural protein.

A mimetic of the peptide can be designed, for example, by using a computerized molecular modeling. To be specific, a mimetic of the peptide can be designed to comprise the structure having one or more peptide bonds substituted with a binding site selected from the group consisting of —CH$_2$NH—, —CH$_2$S—, —CH$_2$—CH$_2$—, —CH═CH— (cis and trans), —CH—CF-(trans), CoCH$_2$—, —CH(OH)CH$_2$—, and —CH$_2$SO—, depending on the cases through a method known in the art. Preferably, the mimetic of the peptide has an improved chemical stability, enhanced pharmacological properties (i.e., half-life, absorption, titer, efficacy, etc.), modified specificity (e.g., a broad spectrum of biological activities), and reduced antigenicity. Also, the mimetic may be prepared at cheaper cost. Preferably, a mimetic of the peptide may comprise a covalent binding with one or more markers or conjugants either directly or through a spacer (e.g., amide group) in a non-interferent site(s) on the expected analogues, through the quantitative structure-activity data and/or molecular modeling. Mostly the non-interferent sites are the sites where a mimetic of the peptide does not directly form a binding site with specific receptor(s), thereby generating therapeutic effects. In addition, a more stable peptide with the intended anti-inflammatory effect can be prepared by systematical substitution of one or more amino acids of the common sequences with D-amino acid of the same type (for example, D-lysine in place of L-lysine).

Those skilled in the art would understand that designing and preparation of the protein comprising a mimetic of the peptide do not require undue trials of experiments. For example, one can refer to the literatures by Ripka et al., Kieber-Emmons et al., or Sanderson [Curr. Opin. Chem. Biol. (1998) 2, 441-452; Curr. Opin, Biotechnol. (1997) 8, 435-441; Med. Res. Rev. (1999) 19179-197].

As another aspect, the present invention provides a method for designing a mimetic of the peptide.

Mode for the Invention

Hereinafter, the present invention is described in more detail through providing following Examples. However, these Examples are merely meant to illustrate, but in no way to limit, the claimed invention.

EXAMPLE 1

Preparation of Peptides

The peptides having the amino acid sequences shown in Table 1 were synthesized by using an automatic peptide synthesizer (Milligen 9050, Millipore, USA), and the synthesized peptides were separated and purified using a C18 reversed-phase high-performance liquid chromatography (HPLC, Waters Associates, USA). ACQUITY UPLC BEH300 C18 (2.1×100 mm, 1.7 μm, Waters Co, USA) was used as a column.

TABLE 1

| SequenceIDNo. | Nameofpeptide | Sequenceofpeptide |
|---|---|---|
| 1 | SIS-1 | MSLPSPRDGRTDGRTDCTR |
| 2 | SIS-1#1 | MSLPSP |
| 3 | SIS-1#2 | RDGRTDG |

TABLE 1-continued

| SequenceIDNo. | Nameofpeptide | Sequenceofpeptide |
|---|---|---|
| 4 | SIS-1#3 | RTDCTR |
| 5 | SIS-1#4 | MSLPSPRDGRTDG |
| 6 | SIS-1#5 | PSPRDG |
| 7 | SIS-1#6 | PSPRDGRTDG |
| 8 | SIS-1#7 | RTDG |
| 9 | SIS-1#8 | RDGRTDGRTD |
| 10 | SIS-1#9 | DGRTDG |
| 11 | SIS-1#10 | GRTDG |
| 12 | SIS-1#11 | TDG |
| 13 | SIS-1#12 | DG |
| 14 | SIS-1#13 | RD |
| 15 | SIS-1#14 | RDG |
| 16 | SIS-1#15 | RDGR |
| 17 | SIS-1#16 | RDGRT |
| 18 | SIS-1#17 | RDGRTD | inflammatory cytokines, the activated pathogenic B cells were treated with each of the 18 types of synthesized novel peptides and the reduction in secretion of inflammatory cytokines from the B cells was monitored.

Specifically, in order to determine whether the novel peptides could weaken the pathogenic B cells which are involved in the development of disease symptoms, the in vitro B cells model which is similar to the joint infiltrative B cells of rheumatoid arthritis was used. The activated pathogenic B cell was generated by stimulating Ebstein Barr virus (EBV)-infected B cells with anti-CD150 antibodies, and the cells were treated with 100 ng/me of each of the 18 types of novel peptide.

In order to confirm the effect of 18 types of novel peptides in reducing inflammatory cytokines, the secretion amount of various cytokines (IL-1A, IL-1B, IL-2, IL-4, IL-5, IL-6, IL-8, IL-10, IL-12A, IL-13, IL-17A, GM-CSF, IL-34) secreted from the activated B cells was measured. The supernatants of B cell culture were analyzed enzyme-linked immunosorbent assay (ELISA), and the difference in absorbance (450 nm-570 nm) of the color developing reagent was measured as test results. Based on the measured difference in absorbance (450 nm-570 nm) of the color developing reagent, the absorbance of cytokines secreted when treated with the 18 types of novel cytokines was calculated in percentage, while setting the absorbance corresponding to the cytokines secreted from the activated B cells stimulated by anti-CD150 as 100%. The reduced percentages of cytokines are shown in Table 2.

TABLE 2

| Sequence ID No. | Name of peptide | Inhibition rate of each cytokine compared to CD150-stimulated EBV-t B cells (%) | | | | | | | | | | | |
|---|---|---|---|---|---|---|---|---|---|---|---|---|---|
| | | IL-1A | IL-1B | IL-2 | IL-4 | IL-5 | IL-6 | IL-8 | IL-10 | IL-12A | IL-13 | IL-17A | IL-34 | GM-CSF |
| 1 | SIS-1 | 22.7 | 25.4 | 19.7 | 59.9 | 30.3 | 42.9 | 53.8 | 47.6 | 43.5 | 37.6 | 63.6 | 43.4 | 60.5 |
| 2 | SIS-1#1 | 7.8 | 9.3 | 13.5 | 19.8 | 18.5 | 19.2 | 17.5 | 7.2 | 19.8 | 15.0 | 24.8 | 18.8 | 18.0 |
| 3 | SIS-1#2 | 23.8 | 18.2 | 15.1 | 23.8 | 25.4 | 29.8 | 25.2 | 19.8 | 30.1 | 23.8 | 39.8 | 25.4 | 19.0 |
| 4 | SIS-1#3 | 14.0 | 20.0 | 12.3 | 13.2 | 17.4 | 18.2 | 19.2 | 25.2 | 19.4 | 10.2 | 11.0 | 9.8 | 7.2 |
| 5 | SIS-1#4 | 18.1 | 16.5 | 18.8 | 20.8 | 20.4 | 32.3 | 32.0 | 18.0 | 33.9 | 23.1 | 43.0 | 16.8 | 18.5 |
| 6 | SIS-1#5 | 8.3 | 14.2 | 6.8 | 13.2 | 9.8 | 18.7 | 10.5 | 7.2 | 8.9 | 15.2 | 12.8 | 13.2 | 7.5 |
| 7 | SIS-1#6 | 12.0 | 15.2 | 23.1 | 20.5 | 15.6 | 33.9 | 28.0 | 4.5 | 30.8 | 29.4 | 42.2 | 31.0 | 21.2 |
| 8 | SIS-1#7 | 6.3 | 5.3 | 7.4 | 10.2 | 3.5 | 11.8 | 3.2 | 5.3 | 11.4 | 3.6 | 9.5 | 2.9 | 4.5 |
| 9 | SIS-1#8 | 30.2 | 25.9 | 33.0 | 18.9 | 12.0 | 23.8 | 29.2 | 10.0 | 19.2 | 33.5 | 30.1 | 19.8 | 19.8 |
| 10 | SIS-1#9 | 20.4 | 18.2 | 15.5 | 16.0 | 16.2 | 18.8 | 15.4 | 14.2 | 20.8 | 13.2 | 9.2 | 15.0 | 15.0 |
| 11 | SIS-1#10 | 7.8 | 4.2 | 11.4 | 19.5 | 24.2 | 25.0 | 17.9 | 7.5 | 29.8 | 25.7 | 25.0 | 27.0 | 13.0 |
| 12 | SIS-1#11 | 6.0 | 2.7 | 3.2 | 19.5 | 10.8 | 8.1 | 4.2 | 4.2 | 6.8 | 5.9 | 6.3 | 7.2 | 4.2 |
| 13 | SIS-1#12 | 0.3 | 1.3 | 1.2 | 1.3 | 0.9 | 3.1 | 0.1 | 0.3 | 2.9 | 0.9 | 0.3 | 0.3 | 1.0 |
| 14 | SIS-1#13 | 1.0 | 1.2 | 1.6 | 1.6 | 2.5 | 1.2 | 0.7 | 1.0 | 1.2 | 0.5 | 0.7 | 0.1 | 0.5 |
| 15 | SIS-1#14 | 7.2 | 5.3 | 10.2 | 3.0 | 11.0 | 1.5 | 5.7 | 10.4 | 2.9 | 4.4 | 7.7 | 4.2 | 0.3 |
| 16 | SIS-1#15 | 11.5 | 5.7 | 12.7 | 6.3 | 6.4 | 4.8 | 15.0 | 7.2 | 10.8 | 7.2 | 10.1 | 6.0 | 1.5 |
| 17 | SIS-1#16 | 16.2 | 17.0 | 15.4 | 23.9 | 20.3 | 22.8 | 33.0 | 31.2 | 29.8 | 24.5 | 32.8 | 23.1 | 6.2 |
| 18 | SIS-1#17 | 18.8 | 20.5 | 17.0 | 32.0 | 14.0 | 16.8 | 22.0 | 15.8 | 16.0 | 14.8 | 23.8 | 20.8 | 14.8 |

EXAMPLE 2

Analysis of Reduction of the Secretion of Inflammatory Cytokines in the Activated B Cells In order to determine the activity of the novel peptides synthesized in Example 1 for reducing the secretion of As a result, it was observed that the secretion of various inflammatory cytokines which was increased in the activated B cells stimulated by anti-CD150 antibody (EBVt-B/anti-CD150) was effectively reduced in the test group treated with the 18 types of novel peptides (EBVt-B/anti-CD150/SIS-1 and 18 kinds of peptides) (Table 2).

These results support that the novel peptides of the present invention effectively reduce the secretion of inflammatory cytokines, thereby treating inflammatory diseases.

EXAMPLE 3

Analysis of the Effects of Alleviating Inflammation Using the TPA-Induced Ear Edema Mouse Model The present inventors confirmed that the peptides of the present invention are effective in alleviating inflammation invivo, along with reduction of the secretion of inflammatory cytokines as confirmed in Example 2. To be specific, in order to identify the anti-inflammatory effect of the peptide SIS-1, which is a representative peptide of 18 types of novel peptides prepared in Example 1, the present inventors used the method for evaluating the mouse ear edema wherein 12-O-tetradecanoylphorbol-13-acetate (TPA) induces acute inflammation as described in the literature (Eur J Pharmacol. 2011: 15; 672(1-3):175-179).

3-1. Preparation of the TPA-Induced Ear Edema Mouse Model and Administration of the Novel Peptides Thereto The TPA-induced ear edema mouse model is an animal model where erythema and edema caused by acute inflammation can be observed and it was prepared by the following method. Detailed test method and test groups are shown in FIG. 1. The 24 mice of 5-week-old ICR mouse (C57BL/6, mal, central laboratory animals, Korea) were divided into 6 mice per group, and their hairs of both ears were removed before applying the sample. Edema was induced by applying 2.5 µg of acetone TPA on the right ear, and the left ear was used as control, by applying the vehicle, for examining the degree of inflammation induced. The drug was administered twice at 0.5 hours to 3 hours after applying TPA. The novel peptide SIS-1 and the control drugs, methotrexate (MTX) and dexamethasone (DEX) were injected intraperitoneally. The control group was treated with phosphate buffered saline (PBS).

3-2. Measurement of the Degree of Intensification

The anti-inflammatory effect of the peptide SIS-1 was determined by observing the degree of edema inhibition as compared to the control group injected with vehicle. After 6 hours of TPA application, pictures of both ears were taken to determine the degree of ear edema, and the degree of inflammation alleviated was determined by measuring the thickness and weight per certain area of ear.

Figure 3:
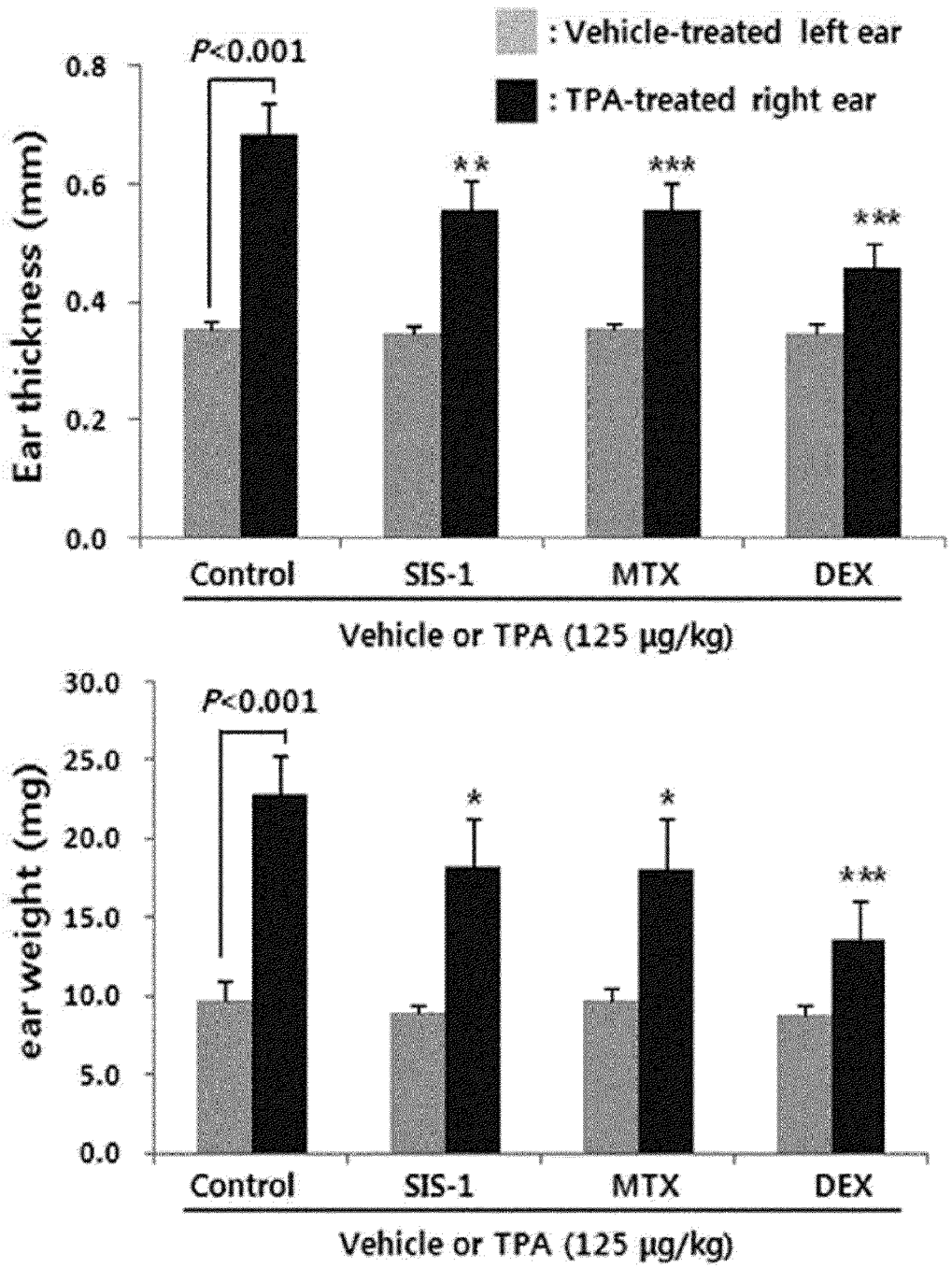
FIG. 3 shows the graph of measurements of mouse ear thickness and weight per specific area to confirm the inflammation alleviating effects in the TPA-induced ear edema mouse model by administration of the peptide SIS-1 of the present invention.

As a result, it was observed that erythema which was increased by TPA application was reduced in the group treated with the peptide SIS-1, and showed similar level of anti-inflammatory effect compared to MTX and DEX, which are the control drugs (FIG. 2). In addition, while edema caused by TPA increases the thickness and weight of ear, the novel peptide SIS-1 inhibited significantly the inflammatory response (FIG. 3).

These results suggest that the novel peptide of the present invention can alleviate inflammation in the actual animal models, thereby treating inflammatory diseases.

EXAMPLE 4

Analysis of Therapeutic Effect of the Novel Peptide for Rheumatoid Arthritis Using the Collagen-Induced Arthritis Mouse Model In order to investigate the therapeutic effect of the peptide SIS-1, which is a representative peptide of the 18 types of novel peptides prepared in Example 1 against a representative autoimmune disease, arthritis, the experiment was performed using the collagen-induced arthritis mouse model of the literature (Nature, 283, pp 666-668, 1980; Arthritis Rheum, 46, pp 793-801, 2002).

4-1. Preparation of the Collagen-Induced Arthritis Mouse Model and Administration of the Novel Peptides Thereto The collagen-induced arthritis (CIA) is the model with arthritis of autoimmune disease type having similar characteristics as human rheumatoid arthritis and it was prepared by the following method.

Detailed test method and test groups are shown in FIG. 4. The 100 µg of bovine type II collagen (Chondrex four, United States) was emulsified by mixing it with Freund's complete adjuvant (Chondrex, USA), and 7-week-old DBA/1 mouse (C57BL/6, male, central laboratory animals, Korea) was immunized by injecting the emulsified collagen solution intradermally at the tail region. On the 14th day of the first immunization, 50 µg of bovine type II collagen (Chondrex four, United States) was emulsified by mixing it with Freund's complete adjuvant (Chondrex, USA), and the second immune (boosting) response was induced by injecting the same intradermally at the tail region.

The novel peptide SIS-1 and a control drug, dexamethasone (DEX), were intraperitoneally administered three times a week from the next day of inducing the second immune response, and the control group (CIA) was treated with PBS.

4-2. Assessment of the Degree of Arthritis Intensification

In order to monitor the development of arthritis, the thickness of foot was measured using loop handle thickness gauge (Mitutoyo) while observing the weight change and the level of pathogenesis. In addition, the severity of the joint inflammation was assessed three times a week by two observers without knowing the contents of the experiment. Assessment of arthritis was performed by adding the scores for four legs per one mouse according to the following criteria, based on the arthritis progression index by Rossoliniec, et al. and then by taking the average of the values measured by two observers. The score and criteria for assessing arthritis are as follows:

0 point: no edema or swelling 1 point: mild edema and redness confined to foot or ankle joint 2 points: mild edema and redness in ankle joint through metatarsal 3 points: moderate edema and redness in ankle joint through metatarsal 4 points: edema and redness through the whole leg, and appearance of acampsia The maximum arthritis index is 4 points per leg, and the maximum disease index per mouse is 16.

As a result, the slight decrease in body weight was observed in the CIA group having arthritis caused by CIA-induction, compared to the normal mice group (Normal) (FIG. 5). This seems to be a natural weight loss incurred by the onset of disease. However, in the group treated with the novel peptide SIS-1, the mouse weight was maintained similar to that of Normal group, which was due to the symptom relief (FIG. 5). Therefore, it was confirmed that the peptides of the present invention could treat arthritis by alleviating weight loss effectively.

Figure 6:
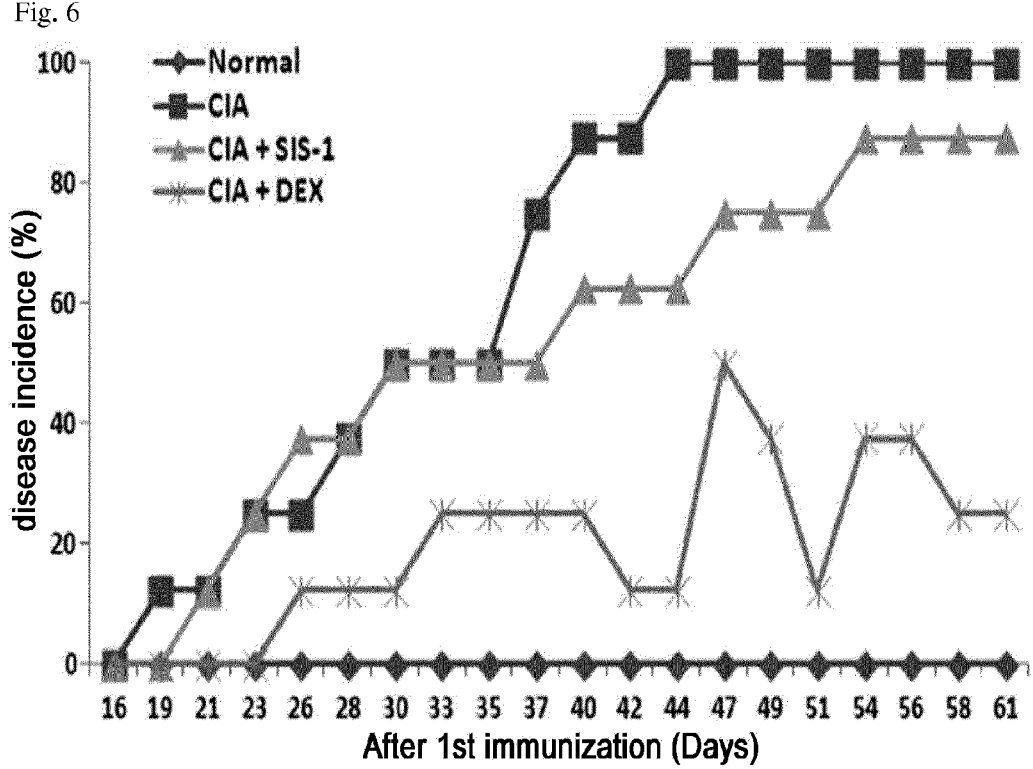
FIG. 6 shows the graph of periodical measurements of the incidence of arthritis after second immunization in the collagen-induced arthritis mouse model.
Figure 7:
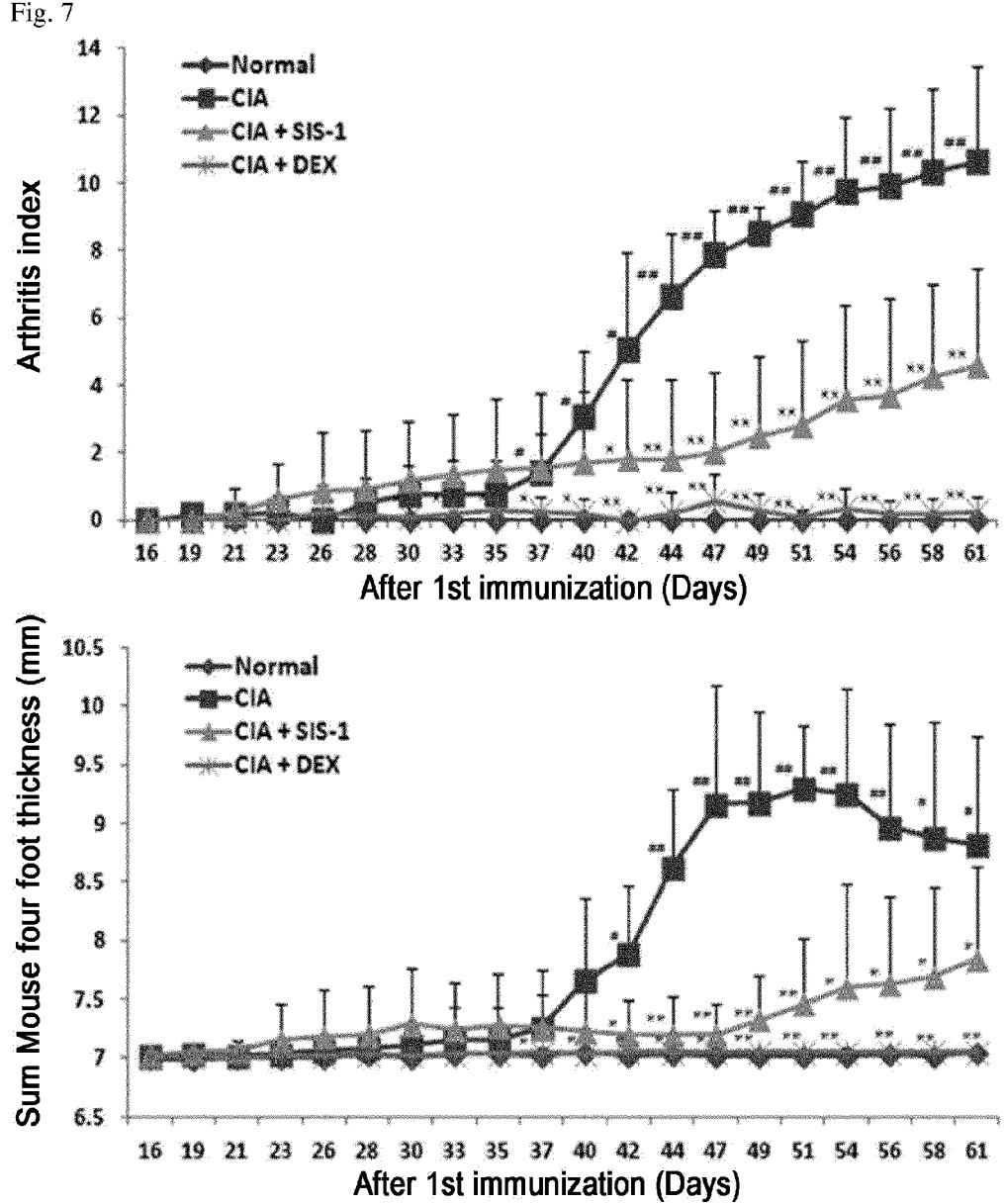
FIG. 7 shows the graph of periodical measurements of arthritis progress index and foot thickness after second immunization, to determine the therapeutic effects of the peptide against rheumatoid arthritis in the collagen-induced arthritis mouse model by administration of the peptide SIS-1 of the present invention.
Figure 8:
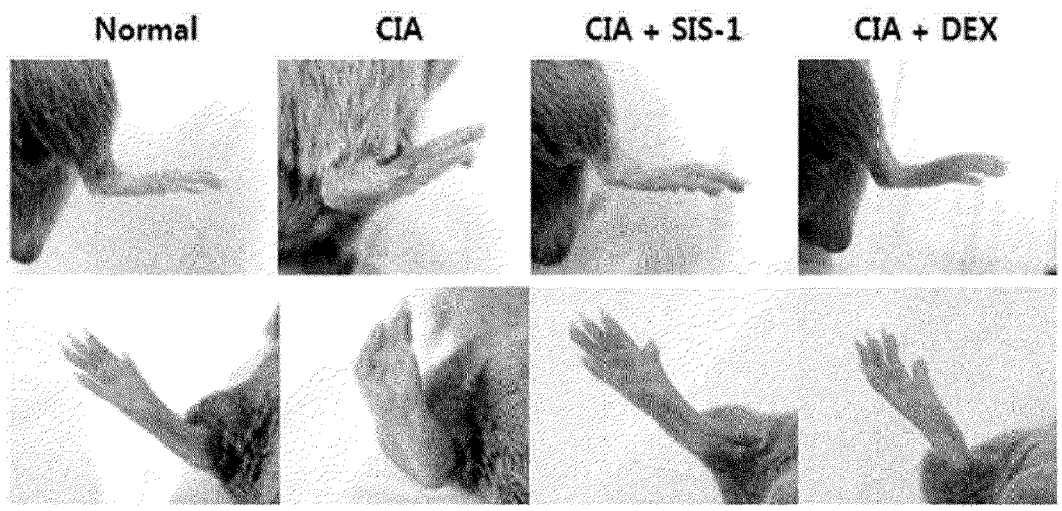
FIG. 8 shows the photographs of the foot joint part right before the completion of collagen-induced arthritis mouse model test to determine the changes of its condition by administration of the peptide SIS-1.
Figure 9:
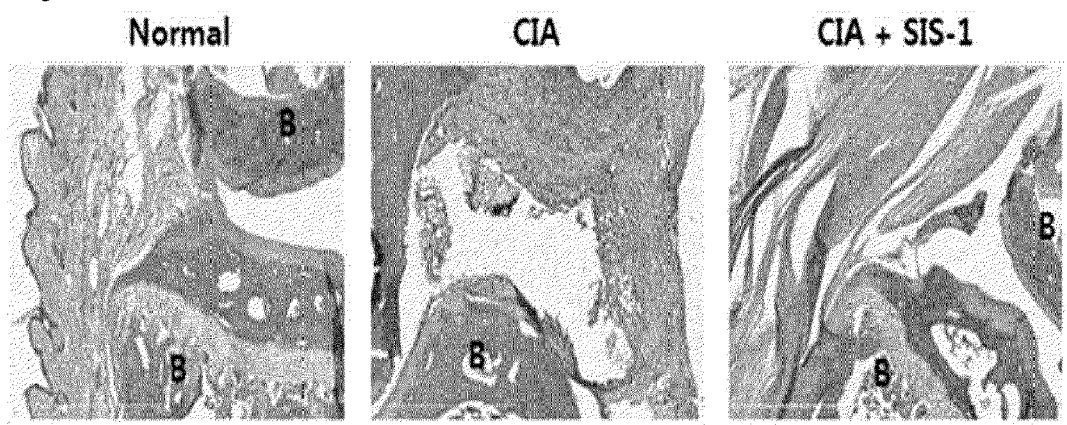
FIG. 9 shows the results of identifying the degree of destruction of foot joint and cartilage tissue by administration of the peptide SIS-1 through staining, after the completion of the collagen-induced arthritis mouse model test.

In addition, for measuring the incidence of arthritis after the second immunization (FIG. 6), when the symptoms appeared even in one of the mouse's feet, the mouse was considered positive for having arthritis. In the CIA group, it was found that arthritis was induced by 100% after approximately 44 days of immunization. On the other hand, in the test group treated with the novel peptide SIS-1, arthritis was induced only by 87.5% by the end of the test and the disease symptom was found to be delayed (FIG. 6). Also, it was identified that treatment with the novel peptide SIS-1 reduced the arthritis progression index and swelling of ankle joints significantly compared to the CIA group (FIGS. 7 and 9).

4-3. Histological Analysis

In order to determine the damage in the cartilage of joints, the histological examination was performed after completion of the test. On the 9th week of the animal model test, after the test animal was killed, the hind leg of the mouse hind was fixed with 10% formalin and coated with paraffin after removing compounds of calcium from the bones. Joint section was prepared and stained with hematoxylin and eosin.

As a result, in the joints of CIA group, infiltration of many immune cells was observed as compared to a normal group, and pannus formation, cartilage destruction, and bone erosion were observed as well. On the other hand, the destruction of joints and cartilage in the mice treated with the novel peptide SIS-1 was maintained at similar level as the normal mice (FIG. 9).

4-4. Serological Analysis (Measurement of Antibodies Specific to Collagen)

In order to determine the therapeutic effect of the novel peptide SIS-1 for arthritis, enzyme-linked immunosorbent assay (ELISA) was performed to measure the antibodies specific to bovine type II collagen with the serological test. As mentioned in the literature, IgG antibody, known as the rheumatoid factor (RF), or subtype of IgG (IgG1 and IgG2a) and IgM autoantibody are known to form immune complexes, cause inflammation, and develop the lesions of rheumatoid arthritis (Journal of Ethnopharmacology 112 (2007) 408).

After diluting the serum of each test group in a ratio of 1:25000 (IgG) or 1:10000 (IgG1, IgG2a, IgM), the titer of serum autoantibody specific to type II collagen was measured.

Figure 10:
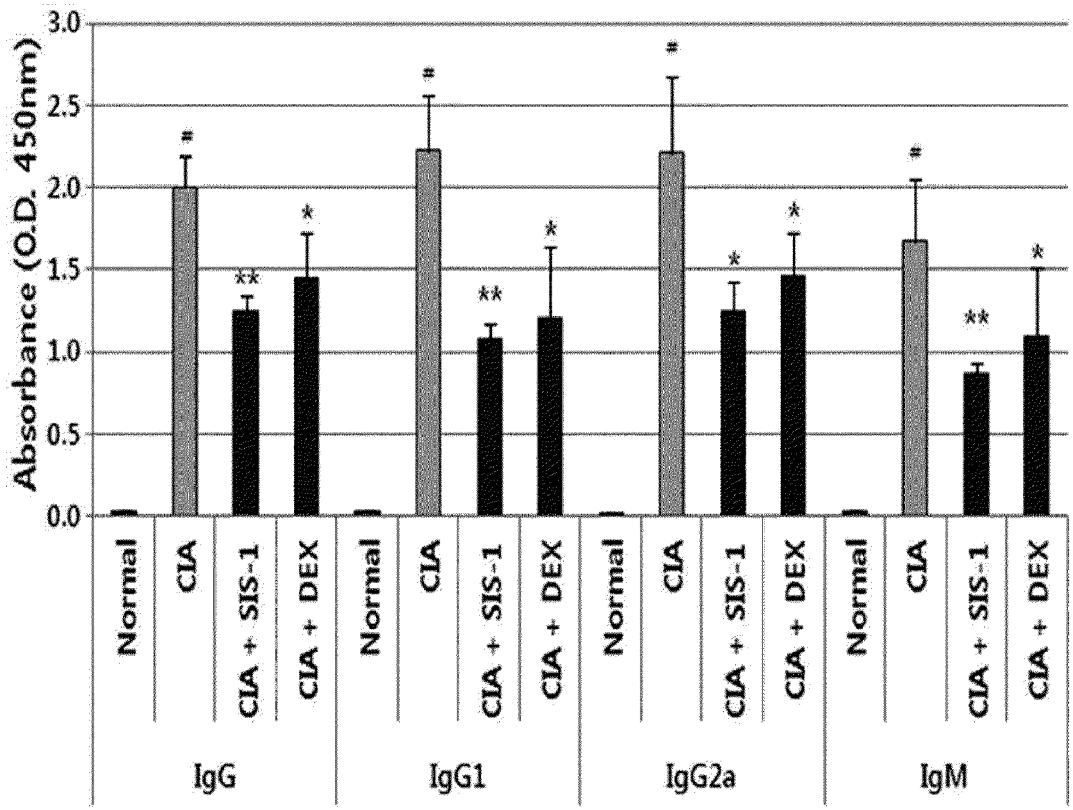
FIG. 10 shows the graph of measurement of the production level of the antibody specific to bovine type II collagen in serum in collagen-induced arthritis mouse model by administration of the peptide SIS-1.

As a result, in the serum of the CIA group with arthritis caused by CIA-induction, it was observed that the level of all the autoantibodies was highly increased. In contrast, in the mice group treated with the novel peptide SIS-1, the generation was decreased significantly by 40 to 50%, which is identified to be as effective as or superior than the group treated with a control drug, DEX (FIG. 10).

These results suggest that the peptides of the present invention provide the effective treatment in animal model having autoimmune diseases, and thus can effectively treat or prevent inflammatory diseases, especially autoimmune diseases.

From the above description, those skilled in the art will understand that the present invention can be carried out in other embodiments without changing the technical principles or essential features. In this regard, the above described examples must be understood as illustrative in every way, not as determinative. The scope of the present invention should be interpreted as comprising any changes or modifications derived from the meaning, scope, and equivalent concept of the following claims, rather than the above detailed description.

The invention claimed is:

1. An isolated peptide represented by an amino acid sequence of SEQ ID NO: 1 or a fragment thereof.

2. The isolated peptide or fragment thereof according to claim 1, wherein the fragment comprises:
   a. 6 to 13 consecutive amino acid residues, comprising the $4^{th}$ to $6^{th}$ amino acids (proline-serine-proline, PSP) of an amino acid sequence of SEQ ID NO: 1;
   b. 4 to 10 consecutive amino acid residues, comprising the $10^{th}$ to $13^{th}$ amino acids (arginine-threonine-aspartic acid-glycine, RTDG) of an amino acid sequence of SEQ ID NO: 1;
   c. 6 to 10 consecutive amino acid residues, comprising the $14^{th}$ to $16^{th}$ amino acids (arginine-threonine-aspartic acid, RTD) of an amino acid sequence of SEQ ID NO: 1;
   d. 2 to 6 consecutive amino acid residues, comprising the $12^{th}$ and $13^{th}$ amino acids (aspartic acid-glycine, DG) of an amino acid sequence of SEQ ID NO: 1; or
   e. 2 to 6 consecutive amino acid residues, comprising the $7^{th}$ and $8^{th}$ amino acids (arginine-aspartic acid, RD) of an amino acid sequence of SEQ ID NO: 1.

3. The isolated peptide or fragment thereof according to claim 2, wherein the fragment is any one of the amino acid sequences selected from the group consisting of SEQ ID NOs: 2 to 18.

4. The isolated peptide or fragment thereof according to claim 1, wherein the peptide or fragment thereof has an anti-inflammatory effect.

5. A polynucleotide encoding the peptide or fragment thereof of claim 1.

6. A pharmaceutical composition for preventing or treating inflammatory disease, comprising the peptide or fragment thereof of claim 1.

7. The composition according to claim 6, which further comprises a pharmaceutically acceptable carrier.

8. The composition according to claim 6, wherein the inflammatory disease is selected from the group consisting of atopy, psoriasis, dermatitis, allergy, arthritis, rhinitis, otitis media, pharyngolaryngitis, tonsillitis, cystitis, nephritis, pelvic inflammatory disease, Crohn's disease, ulcerative colitis, ankylosing spondylitis, systemic lupus erythematodes (SLE), atherosclerosis, asthma, arteriosclerosis, edema, rheumatoid arthritis, delayed allergy (IV-type allergy), graft rejection, graft-versus-host disease, autoimmune encephalomyelitis, multiple sclerosis, inflammatory bowel disease, cystic fibrosis, diabetic retinopathy, ischemia-reperfusion injury, restenosis, glomerulonephritis and gastrointestinal allergy.

9. An anti-inflammatory drug, comprising the peptide or fragment thereof of claim 1.

10. An over-the-counter (OTC) drug composition for preventing or ameliorating inflammation, comprising the peptide or fragment thereof of claim 1.

11. A health food composition for alleviating or ameliorating inflammation, comprising the peptide or fragment thereof of claim 1.

12. A cosmetic composition for preventing or alleviating inflammation, comprising the peptide or fragment thereof of claim 1.

13. A method for treating inflammatory disease, comprising administrating the composition of claim 6 to a subject suspected of having inflammatory disease.

14. A method for preparing a mimetic of the peptide of claim 1, comprising designing a mimetic of peptide with an anti-inflammatory activity based on the peptide or fragment thereof of claim 1; and
   a. synthesizing the designed mimetic of peptide.

15. A method for designing a mimetic of the peptide with an anti-inflammatory activity from the peptide or fragment thereof of claim 1.

* * * * *